(12) United States Patent
Nikolchev et al.

(10) Patent No.: US 6,871,650 B1
(45) Date of Patent: Mar. 29, 2005

(54) CONTRACEPTIVE TRANSCERVICAL FALLOPIAN TUBE OCCLUSION DEVICES AND THEIR DELIVERY

(75) Inventors: Julian Nikolchev, Portola Valley, CA (US); Dai Ton, San Jose, CA (US); Amy Thurmond, Portland, OR (US)

(73) Assignee: Conceptus, Inc., San Carlos, CA (US)

( * ) Notice: Subject to any disclaimer, the term of this patent is extended or adjusted under 35 U.S.C. 154(b) by 0 days.

(21) Appl. No.: 09/591,874

(22) Filed: Jun. 12, 2000

Related U.S. Application Data

(63) Continuation of application No. 08/474,779, filed on Jun. 7, 1995, now Pat. No. 6,176,240.

(51) Int. Cl.[7] .................................................. A61F 6/06
(52) U.S. Cl. ...................................... 128/830; 128/831
(58) Field of Search ................................ 128/830–841; 606/151, 191

(56) References Cited

U.S. PATENT DOCUMENTS

| | | | | |
|---|---|---|---|---|
| 3,805,767 A | * | 4/1974 | Erd ............................. | 228/831 |
| 4,700,701 A | * | 10/1987 | Montaldi ..................... | 128/831 |
| 4,994,069 A | * | 2/1991 | Ritchart et al. ............. | 606/121 |
| 5,176,692 A | | 1/1993 | Wilk et al. | |
| 5,377,668 A | * | 1/1995 | Ehmsen et al. ................ | 128/4 |
| 5,499,995 A | | 3/1996 | Teirstein | |
| 5,755,773 A | | 5/1998 | Evans et al. | |
| 5,843,158 A | | 12/1998 | Lenker et al. | |
| 5,935,137 A | * | 8/1999 | Saadat ......................... | 128/831 |
| 5,954,715 A | * | 9/1999 | Harrington ................... | 606/28 |
| 5,976,162 A | * | 11/1999 | Doan ........................... | 128/831 |
| 6,068,626 A | * | 5/2000 | Harrington et al. ......... | 128/831 |
| 6,143,007 A | * | 11/2000 | Mariant et al. .............. | 606/151 |
| 6,432,116 B1 | | 8/2002 | Callister et al. | |
| 2002/0013589 A1 | | 1/2002 | Callister et al. | |

* cited by examiner

*Primary Examiner*—Michael A. Brown
(74) *Attorney, Agent, or Firm*—Townsend and Townsend and Crew LLP; Lynn Thompson

(57) ABSTRACT

The invention provides intrafallopian devices and non-surgical methods for their placement to prevent conception. The efficacy of the device is enhanced by forming the structure at least in part from copper or a copper alloy. The device is anchored within the fallopian tube by imposing a secondary shape on a resilient structure, the secondary shape having a larger cross-section than the fallopian tube. The resilient structure is restrained in a straight configuration and transcervically inserted within the fallopian tube, where it is released. The resilient structure is then restrained by the walls of the fallopian tube, imposing anchoring forces as it tries to resume the secondary shape.

4 Claims, 4 Drawing Sheets

CONTRACEPTIVE TRANSCERVICAL FALLOPIAN TUBE OCCLUSION DEVICES AND THEIR DELIVERY

CROSS-REFERENCES TO RELATED APPLICATIONS

This application is a continuation of, and claims the benefit of priority from U.S. patent application Ser. No. 08/474,779, filed Jun. 7, 1995 now U.S. Pat. No. 6,176,240 the full disclosure of which are incorporated herein by reference.

BACKGROUND OF THE INVENTION

1. Field of the Invention

The present invention relates generally to contraception, and more particularly to intrafallopian contraceptive devices and nonsurgical methods for their delivery.

Worldwide demand exists for safe, effective methods of both contraception and permanent sterilization. Although a variety of contraception and sterilization methods are available, all of the existing methods have limitations and disadvantages. Thus, the need for additional safe, low cost, reliable methods of contraception and permanent sterilization, both in developed and less developed countries, is widely recognized.

Many presently available contraception methods require significant user involvement, and user non-compliance results in quite high rates of failure. While the theoretical effectiveness of existing contraceptives, including barrier methods and hormonal therapies, is well established, overcoming user noncompliance to improve overall efficacy has proven difficult.

One form of contraception which is less susceptible to user noncompliance is the intrauterine device (IUD). IUDs have been found to have higher rates of reliability, and are effective for a longer period of time, than most other commercially available contraceptives. Unfortunately, IUDs are also associated with serious infectious complications. For this reason, the use of IUDs within the United States has decreased dramatically. Additionally, IUDs are subject to unplanned expulsion, and must be removed due to excessive pain or bleeding in a percentage of cases, further reducing the acceptance of the IUD as a contraceptive method. Interestingly, the efficacy of copper IUDs appears to be higher than that of non-metallic IUDs. The reason for this has not been fully explained.

Commercially available options for permanent sterilization include fallopian tube ligation and vasectomy. These methods are surgical, are difficult to reverse, and are not available to many people in the world. It is common knowledge that fertilization occurs in the fallopian tubes where the sperm and ovum meet. Tubal ligation avoids this by complete occlusion of the fallopian tubes.

It has previously been proposed to reversibly occlude the fallopian tubes, for example, by in vitro formation of an elastomeric plug, or otherwise anchoring a device on either side of the narrowest region of fallopian tube, called the "isthmus." Such fallopian tube occlusion methods appear promising; however, an unacceptably high percentage of the non-surgical devices proposed to date have become dislodged during previous studies. Even where non-surgical intrafallopian devices have remained in place, they have been found to be only moderately effective at preventing conception.

For these reasons, it would be desirable to provide effective, reliable intrafallopian devices for contraception and sterilization. It would be particularly desirable to provide highly effective intrafallopian devices which did not require surgery for placement. It would be especially desirable if such devices and methods allowed easy placement of the device, but were less susceptible to being dislodged than previously proposed non-surgical intrafallopian devices.

2. Description of the Related Art

The experimental use of a stainless steel intrafallopian device is described in Transcatheter Tubal Sterilization in Rabbits, Penny L. Ross, RT 29 "Investigative Radiology", pp. 570–573 (1994). The experimental use of an electrolytically pure copper wire as a surgical contraceptive intrafallopian device in rats was described in "Antifertility Effect of an Intrafallopian Tubal Copper Device", D. N. Gupta, 14 Indian Journal of Experimental Biology, pp. 316–319 (May 1976).

U.K. Patent Application Pub. No. 2,211,095 describes a uterine screw plug for blocking the fallopian tube. European Patent Application Pub. No. 0,010,812 describes a device for placement in the oviducts having enlargements at either end for anchoring the device. The same device appears to be described in Netherlands Patent No. 7,810,696.

The use of tubal occlusion devices is described in "Hysteroscopic Oviduct Blocking With Formed-in-Place Silicone Rubber Plugs", Robert A. Erb, Ph.D., et al., The Journal of Reproductive Medicine, pp. 65–68 (August 1979). A formed-in-place elastomeric tubal occlusion device is described in U.S. Pat. No. 3,805,767, issued to Erb. U.S. Pat. No. 5,065,751, issued to Wolf, describes a method and apparatus for reversibly occluding a biological tube. U.S. Pat. No. 4,612,924, issued to Cimber, describes an intrauterine contraceptive device which seals the mouths of the fallopian tubes.

German Patent No. 28 03 685, issued to Brundin, describes a device for plugging a body duct with a device which swells when in contact with a body fluid.

Alternative contraceptive devices are disclosed in copending U.S. patent application Ser. No. 08/475,252, filed Jun. 7, 1995, the full disclosure of which is herein incorporated by reference.

SUMMARY OF THE INVENTION

The present invention provides intrafallopian devices and methods for their placement to prevent conception. The intrafallopian devices of the present invention are transcervically delivered, resiliently anchored structures which are formed at least in part from copper to provide long term contraception, or alternatively permanent sterilization, without the need for surgical procedures or the increased bleeding, pain, and risks of infection associated with intrauterine devices (IUDs).

The use of copper in the intrafallopian device of the present invention improves its efficacy as a contraceptive method. Devices formed from plastically deformable materials, however, are less readily restrained in the fallopian tube. Apparently, the large variation in the actual shape and dimensions of fallopian tubes does not provide reliable anchoring for a pre-formed deformable intrafallopian device. The intrafallopian device of the present invention therefore comprises a resilient structure, usually a metallic coil, which includes a copper alloy, a copper plating, or copper fibers, ideally comprising an alloy including at least 75% copper. The coil material typically includes beryllium, zinc, stainless steel, platinum, a shape memory alloy such as Nitinol™, or the like. Preferably, the coil is composed of an alloy of beryllium and copper. Although the present device will generally result in occlusion, it need not completely occlude the fallopian tube to prevent the meeting of the sperm and ovum. Instead, the presence of the copper on the resilient structure is sufficient to provide effective contraception.

Conveniently, the present invention further comprises non-surgical placement of such intrafallopian devices by transcervical introduction. The resilient structure is restrainable in a straight configuration, e.g., by inserting the device within a catheter, greatly facilitating and reducing the risks of introduction. Thus, the cost and dangers associated with existing surgical contraceptive and sterilization procedures are avoided.

In a first aspect, a contraceptive intrafallopian device according to the present invention comprises a resilient structure having a proximal end and a distal end. The resilient structure comprises copper, and is biased to form at least one bend near the proximal end of the primary coil. Similarly, the resilient structure is also biased to form at least one bend near its distal end. These proximal and distal bends define an isthmus-traversing region therebetween. Preferably, the isthmus-traversing region also includes at least one bend, thereby helping to anchor the coil within the fallopian tube.

Generally, the resilient structure of the present intrafallopian device will be formed as a primary coil. To help restrain the coil within the fallopian tube, fibers are attached to some embodiments of the coil, the fibers optionally comprising a polyester material such as Rayon™, Dacron™, or the like. Alternatively, copper fibers may be used to increase the exposed copper surface area, the copper fibers generally having a diameter on the order of 0.001 inches.

The bends of the present intrafallopian device are generally formed as a secondary shape imposed on a primary coil. The primary coil is most easily formed as a straight cylindrical coil. The secondary shape will be imposed on the primary coil by bending, optionally heat treating the primary coil while bent. The individual bends may take a wide variety of forms, including sinusoidal curves, the individual loops of a continuous secondary coil, or the like. However, the secondary shape generally defines an overall width which is larger than the fallopian tube, so that the tubal wall restrains the resilient structure when it is released.

Preferably, each of the bends of the present intrafallopian device forms a loop in the primary coil when in a relaxed state. Ideally, the loops are separated by straight sections of coil. The alternating of loops with straight sections of coil forms a large diameter "flower coil," which provides a large relaxed overall width, and also features bends of tight radius, both of which promote retention. Conveniently, the primary coil generally has a diameter less than that of the fallopian tube, and can be restrained in a straight configuration for placement within the fallopian tube, typically by inserting the primary coil within a delivery catheter.

In another aspect, a contraceptive intrafallopian device according to the present invention comprises a resilient primary coil having a primary coil diameter. The primary coil comprises copper, and forms a secondary shape when in a relaxed state. The secondary shape defines a plurality of bends and an overall width which is larger than the primary coil diameter. Thus the primary coil can be easily anchored in a fallopian tube which is smaller in diameter than the secondary shape. Preferably, the present device reacts with a force sufficient to prevent axial movement of the device within the fallopian tube when restrained in a lumen having a diameter in the range between 0.5 mm and 3 mm. The actual anchoring force will depend on the shape of the coil and the modulus of elasticity of the material used.

In yet another aspect, a intrafallopian contraceptive delivery system according to the present invention comprises an elongate body in which the resilient primary coil described above is slidably disposed. A shaft is also slidably disposed within the elongate body and is located proximally of the primary coil. The distal end of the shaft includes a coil interface surface, while the elongate body restrains the primary coil in a straight configuration.

Preferably, a bend in the isthmus-traversing region of the present intrafallopian device, together with the proximal and distal anchor bends, restrains the resilient structure within the isthmus of the fallopian tube. The distal anchor is inserted into the ampulla, distal of the isthmus, while the proximal anchor is located in the ostium, proximal of the isthmus. Unintended movement of the device is further avoided by locating the isthmus-traversing region within the isthmus to resiliently impose anchoring forces against the tubal wall.

In a still further aspect, an intrafallopian contraceptive method according to the principles of the present invention comprises restraining a resilient structure in a straight configuration and transcervically inserting the resilient structure into a fallopian tube. The resilient structure is affixed within the isthmus by releasing a bent isthmus-traversing region. The bend of the isthmus-traversing region exerts a force against the wall of the fallopian tube, anchoring the device within the isthmus. Preferably, a distal anchor on the resilient structure is released distally of the isthmus, and a proximal anchor is released proximally of the isthmus, the distal and proximal anchors generally formed from bends in the resilient structure. Optionally, an electric current is applied through the resilient structure to the fallopian tube, thereby effecting permanent sterilization.

DESCRIPTION OF THE SPECIFIC EMBODIMENTS

Figure 2:
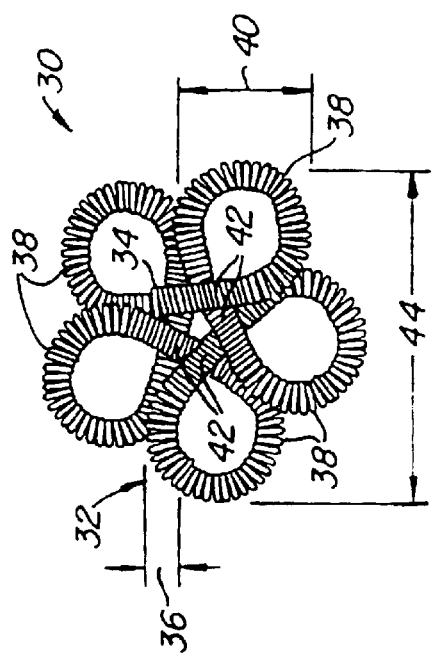
FIG. 2 illustrates an alternative embodiment of a contraceptive intrafallopian device according to the present invention having a plurality of loops which may act as proximal, distal, or lumen anchors.

The present invention encompasses a contraceptive intrafallopian device which can alternatively be used as both a permanent and a reversible means of contraception. The present contraceptive methods and devices minimize the danger of non-use which has limited the efficacy of prior art contraceptive techniques. Moreover, the location of the present devices within the fallopian tubes provides a reduced risk of the infectious complications, increased bleeding, and pelvic pain associated with intrauterine devices (IUDs). Furthermore, the location and the novel shape of the present intrafallopian device provides significant advantages over IUDs, which have been found to be susceptible to unplanned expulsion and removal due to excessive pain and bleeding. The present invention takes advantage of the increase in effectiveness associated with copper IUDs, providing a resilient structure including copper which may be transcervically positioned without the need for surgery.

Although the present contraceptive method may be included within a group of contraceptive techniques generally referred to as fallopian tube occlusion methods, the present invention does not necessarily rely solely on blocking the fallopian tube to prevent fertilization. Instead, contraception is apparently provided by disrupting of ovum transport, the process of fertilization, and/or cleavage of the ovum. While the effect that copper has on these processes is not fully understood, it does appear that copper intrafallopian devices offer potentially significant increases in effectiveness over intrafallopian devices formed of other materials. Optionally, the present invention further encompasses devices which promote tissue growth within the tube to induce tubal occlusion, further inhibiting conception.

The present invention is anchored within the isthmus of the fallopian tube, overcoming the unintended expulsion of the device and the resulting failure of the contraceptive method. Such intrafallopian device expulsion has been the single greatest factor limiting the efficacy of easily positioned intrafallopian contraceptive techniques.

The present intrafallopian devices are generally elongate resilient structures pre-formed into secondary shapes. These secondary shapes will bias the resilient structure so as to provide strong forces against the lumen wall of the fallopian tube. Clearly, the secondary shape must have a larger outer diameter than the inner diameter of the fallopian tube.

Conveniently, the present resilient structures are insertable into a catheter, the catheter wall restraining the resilient structure in a straight configuration. As the resilient structure has an outer diameter when in the straight configuration which is less than the inner diameter of the fallopian tube, the catheter containing the present intrafallopian device is easily transcervically introduced. Moreover, the device is readily removed by snaring the resilient structure near the proximal end and pulling proximally on the resilient structure, thereby straightening the resilient structure and allowing it to be withdrawn without injuring the fallopian tube. Alternatively, an electrical current is applied to the device after it is at least partially releasing the fallopian tube, providing permanent sterilization.

Figure 1:
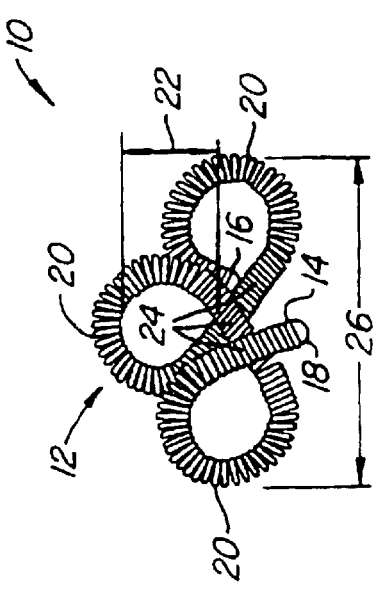
FIG. 1 illustrates a first embodiment of a contraceptive intrafallopian device according to the present invention having a single distal anchor loop, a single proximal anchor loop, and an isthmus-traversing region having a single loop for anchoring the device within the fallopian tube.

Referring now to FIG. 1, a first embodiment of the present contraceptive intrafallopian device 10 is formed from a resilient primary coil 12. Primary coil 12 is most easily originally formed as a straight cylindrical coil or spring, preferably having an outer diameter in the range from 0.2 mm to 5 mm, and having a length in the range from 20 mm to 150 mm. Ideally, primary coil 12 has an outer diameter in the range from 0.4 mm to 2 mm and a length in the range from 30 mm to 70 mm. The straight primary coil may then be bent into a variety of secondary shapes.

The primary coil 12 of intrafallopian device 10 includes a proximal end 14 and a distal end 16. Between these ends, three loops 20 are formed, each having an inner diameter 22. Located between loops 20 are straight sections 24, which increase the overall cross-section of the intrafallopian device to an overall width 26. Preferably, inner diameter 22 is in the range from 2 mm to 10 mm, while overall width 26 is at least 6 mm, ideally being in the range from 8 mm to 40 mm. Distal and proximal ends 14, 16 each include an atraumatic endcap 18 to prevent injury to the fallopian tube.

Preferably, primary coil 12 is formed from a beryllium copper alloy wire. Beryllium copper provides the resilience necessary to avoid expulsion of the device, and also provides the increased effectiveness of a copper contraceptive intrafallopian device. Alternatively, primary coil 12 is formed from a resilient metal, such as stainless steel, platinum, a shape memory alloy, or the like. If such materials are used, primary coil 12 is preferably plated with copper or a copper alloy or otherwise has copper attached.

To further reduce the possibility of expulsion of intrafallopian device 10, fibers are optionally carried on primary coil 12. The fibers may be short individual fibers, or may alternatively be wound into primary coil 12. Preferably, the fibers comprise copper, thereby increasing the total copper surface area. Such copper fibers are preferably bonded to primary coil 12 with solder, brazing, a polymeric adhesive, or the like. Alternatively, polyester fibers such as Dacron™, Rayon™, or the like, are bonded to the surface of primary coil 12 using a polymeric adhesive. The polyester fibers promote increased tissue growth around the coil, thus further reducing the possibility of expulsion of the device from the fallopian tube.

A secondary shape has been superimposed on the primary coil to form intrafallopian device 10, the secondary shape comprising loops 20 separated by straight sections 24. This secondary shape is herein referred to as a "flower coil." The flower coil shape is particularly advantageous in that outer diameter 26 is substantially larger than the primary coil diameter, while the individual loops 20 have relatively small inner diameters 22 which will maintain the largest possible anchoring force against the fallopian tube. Minimizing inner diameter 22 also ensures that anchoring force is applied within the fallopian tube, despite the curvature of the fallopian tube.

Referring now to FIG. 2, an alternative embodiment of the present contraceptive intrafallopian device 30 includes additional loops to ensure anchoring of the device within the fallopian tube. Alternative embodiment 30 is formed from an elongate primary coil 32 having a proximal end 34 and a distal end (not shown). Elongate primary coil 32 has an outer diameter 36 which is smaller than the isthmus of the fallopian tube, allowing the straightened intrafallopian device to be inserted easily. Elongate primary coil 32 has been bent to form a secondary shape including a larger number of loops 38 than the embodiment of FIG. 1. Loops 38 have an outer diameter 40 which is larger than the inner diameter of the fallopian tube, preventing loops 38 from assuming their relaxed shape. Loops 38 are again separated by straight sections 42 of elongate primary coil 32, increasing the overall intrafallopian device diameter 44.

In both embodiments of the present intrafallopian device 10, 30, at least one loop adjacent to the proximal end is disposed proximally of the narrowest portion of the fallopian tube, referred to as the isthmus. Similarly, at least one loop of the intrafallopian device is disposed distally of the isthmus. These proximal and distal loops act as anchors, helping to prevent proximal or distal movement of the intrafallopian device. In the embodiment of FIG. 2, at least one loop is also disposed adjacent to the isthmus of the fallopian tube, further helping to prevent unintentional expulsion.

Alternative intrafallopian device 30 may be positioned with multiple loops acting as proximal or distal anchors, or may alternatively have all but the proximal and distal anchor loops disposed along the fallopian tube to act as anchors within the lumen of that body. Advantageously, the embodiment of FIG. 2 is therefore less sensitive to variations in total fallopian tube length.

Figure 3:
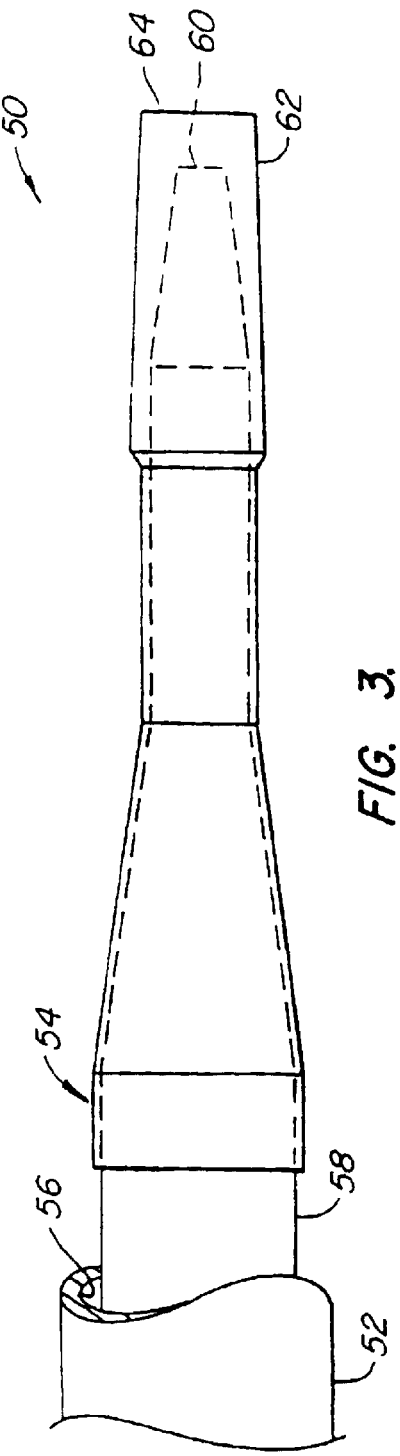
FIG. 3 illustrates the distal portion of a delivery catheter for placement of a contraceptive intrafallopian device according to the present invention.

Referring now to FIG. 3, a delivery catheter for the present intrafallopian device comprises an elongate body 52 and a shaft 54. Elongate body 52 includes a lumen 56 in which shaft 54 is disposed, shaft 54 being slidable in the axial direction. Shaft 54 includes a core 58 having a tapered distal end 60, allowing the device to navigate through tortuous bends while retaining the column strength required to advance the device. Core 58 extends proximally through elongate body 52, and is capable of transferring compressive forces through the elongate body. Core 58 is typically formed from stainless steel, a stainless alloy, or the like. Disposed over distal end 60 of core 58 is pusher cap 62. Pusher cap 62 provides a low friction, deformable end piece having a distal coil interface surface 64. Pusher cap 62 is preferably formed of a low friction polymer such as PTFE, or the like.

Intrafallopian delivery catheter 50 receives the present intrafallopian device within the distal end of lumen 56 of elongate body 52. Lumen 56 has an inner diameter which is slightly larger than outer diameter 36 of the primary coil. The present intrafallopian device is therefore straightened to a straight configuration as it is loaded proximally into the distal end of lumen 56. Elongate body 52 is sufficiently strong to restrain the primary coil in the straight configuration, but must remain sufficiently flexible to allow maneuvering within the body lumen. Elongate body 52 is preferably formed from an inelastic, flexible material such as polyurethane, PET, or the like.

Figure 4:
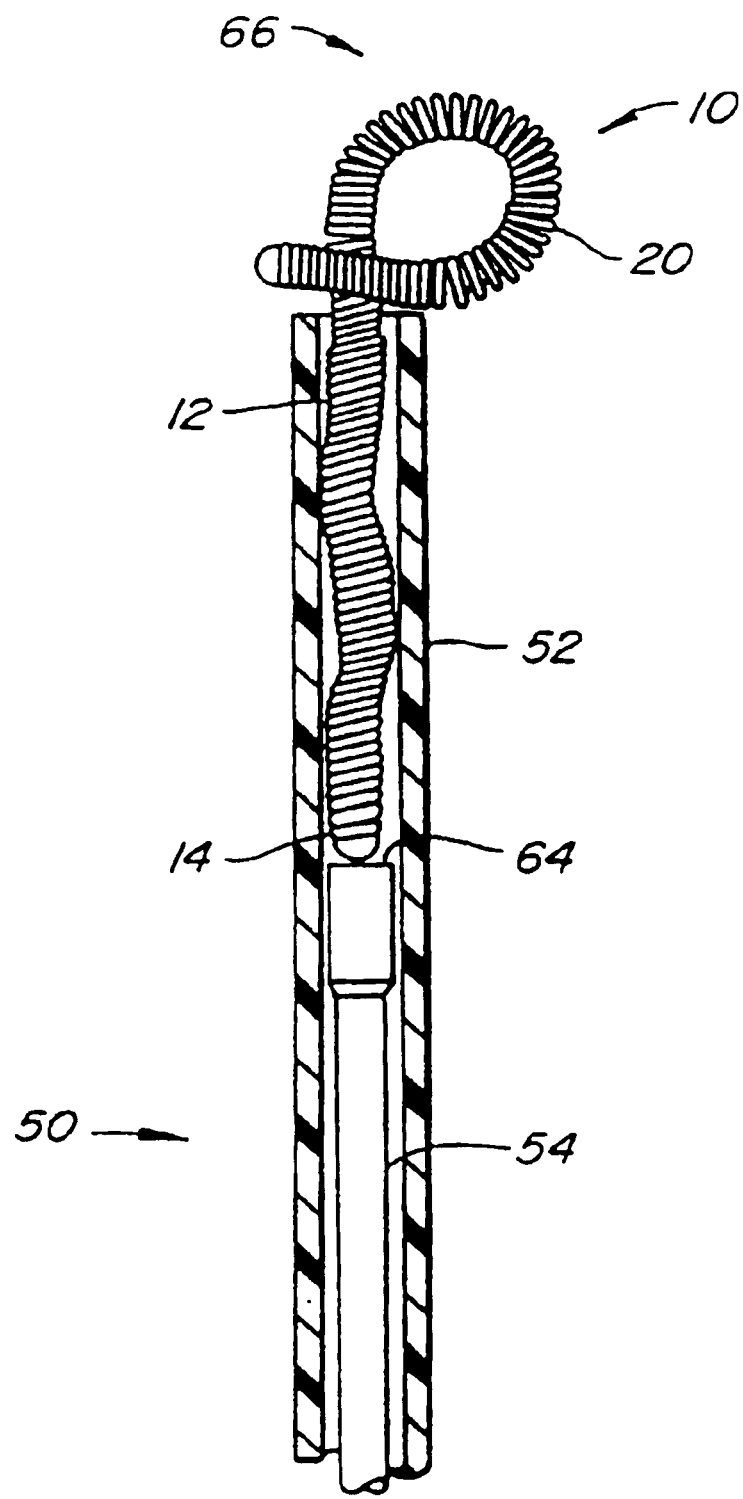
FIG. 4 illustrates the contraceptive intrafallopian device of FIG. 1 partially released from the delivery catheter of FIG. 3.

Referring now to FIG. 4, intrafallopian device 10 is released from delivery catheter 50 within the fallopian tube by holding shaft 54 while proximally withdrawing elongate body 52. Distal coil interface surface 64 engages the proximal end 14 of primary coil 12. Initially, primary coil 12 is restrained in a straight configuration by elongate body 52. As elongate body 52 is withdrawn, primary coil 12 is released. When primary coil 12 is unrestrained it forms loop 20; when released within the fallopian tube it will generally be restrained by the tubal wall in a configuration between straight and the relaxed secondary shape. Preferably, the first loop released will form a distal anchor bend 66. Subsequent loops will bias primary coil 12 against the fallopian tube, and form a proximal anchor bend, in that order.

Figure 5:
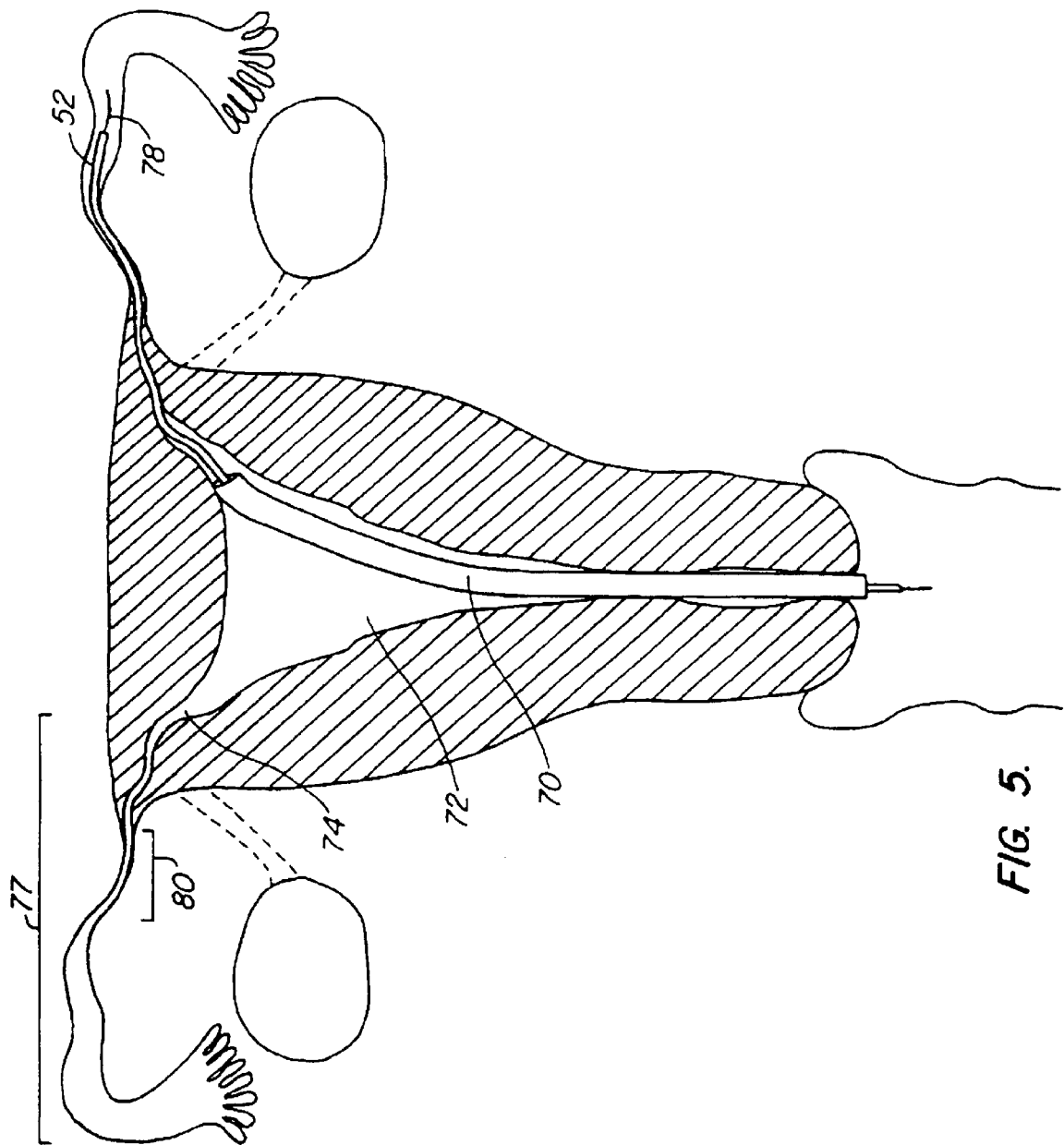
FIGS. 5 and 6 illustrate a contraceptive method using an intrafallopian device according to the principles of the present invention.
Figure 6:
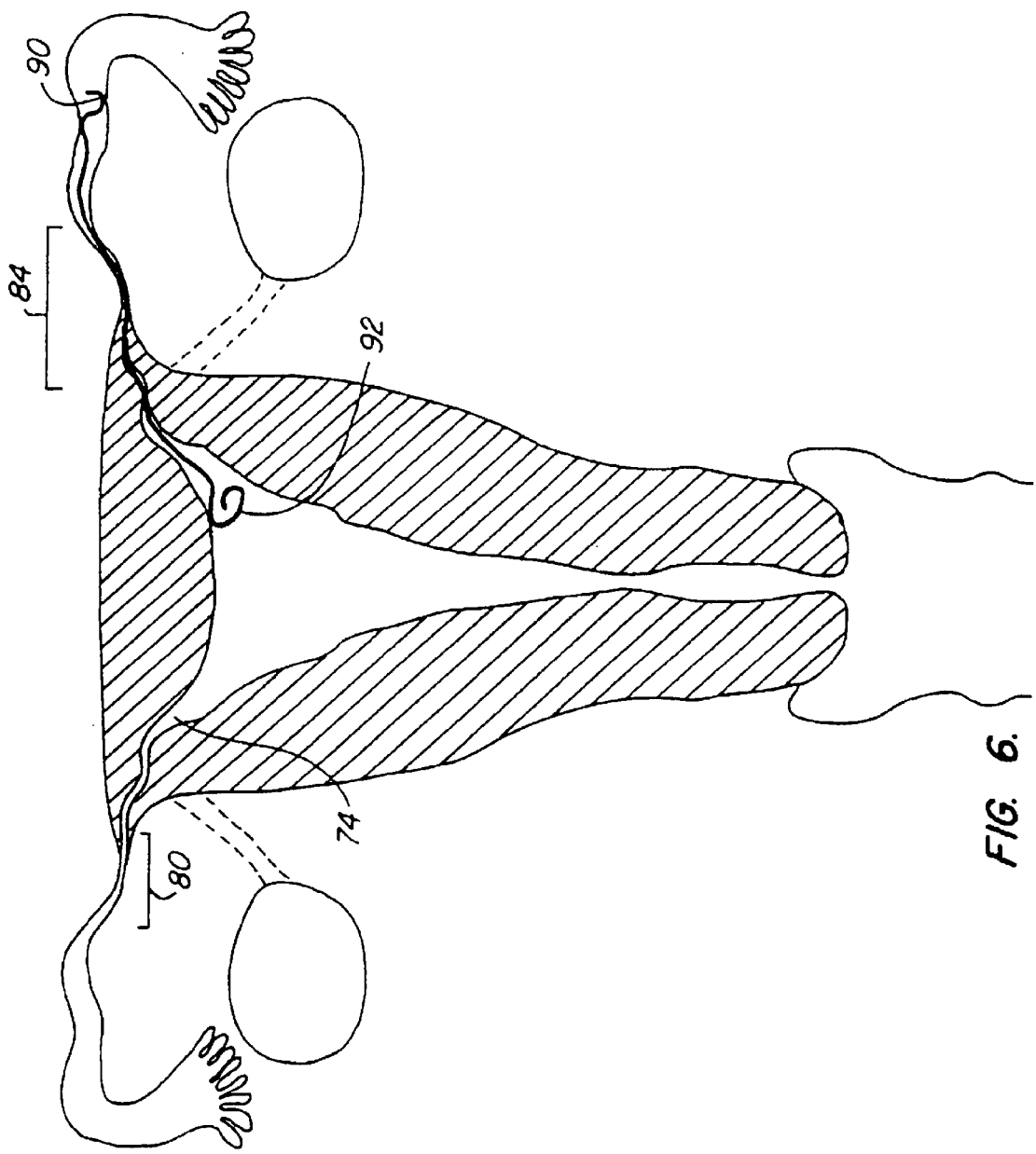

Use of the present contraceptive intrafallopian device will be described with reference to FIGS. 5 and 6. A uterine introducer canula 70 is inserted transcervically through a uterus 72 to the region of an ostium 74. Elongate body 52 is then extended distally from canula 70 into a fallopian tube 77, preferably guided under fluoroscopy. Alternatively, a hysteroscope may be used in place of canula 70. Elongate body 52 is maneuvered using a guide wire 78 past an isthmus 80.

After elongate body 52 extends past isthmus 80, guide wire 78 is removed. An intrafallopian device according to the present invention is inserted in the proximal end of elongate body 52, the intrafallopian device being restrained in a straight configuration by the elongate body. The device is advanced distally using shaft 54, the shaft and elongate body forming delivery catheter 50 (FIG. 3). Delivery catheter 50 is axially positioned so that at least one loop of the intrafallopian device is within a target region 84 adjacent to isthmus 80. Preferably, at least one loop is distal of target region 84, and at least one loop is proximal of target region 84 to form the distal and proximal anchor bends of the implanted intrafallopian device.

Once delivery catheter 50 is properly positioned, elongate body 52 may be axially withdrawn. Shaft 54 axially restrains the intrafallopian device at the target location during withdrawal of elongate body 52, as described regarding FIG. 4. As the distal end of the primary coil is released, the distal loop forms a distal anchor bend 90. Similarly, the proximal loop forms a proximal anchor bend 92. Intermediate loops are restrained within the narrow target region 84, exerting substantial anchoring forces against the walls of the fallopian tube. As seen in FIG. 6, the loops need not assume their relaxed form to provide effective distal or proximal anchors.

The present invention further encompasses permanent sterilization by passing a current through the shaft to the intrafallopian device after elongate body 52 has been partially withdrawn, but before the intrafallopian device is fully released. Fallopian tube tissue in contact with the intrafallopian device is dessechated, and thus attached to the present intrafallopian device. This action also causes permanent tubal damage, leading to the formation of scar tissue which encapsulates the intrafallopian device and causes permanent occlusion of the tubal lumen. Clearly, the resilient member/shaft interface must be conductive to allow the present non-surgical method of permanent sterilization.

In conclusion, the present invention provides a contraceptive intrafallopian device which may be positioned without surgery. While the above is a complete description of the preferred embodiments of the invention, various alternatives, modifications, and equivalents may be used. For example, a wide variety of secondary shapes, including open loops, continuous bends, sinusoidal curves, or the like, may be imposed on the primary coil. Therefore, the above description should not be taken as limiting the scope of the invention, which is defined instead solely by the appended claims.

What is claimed is:

1. A system for providing permanent sterilization, the system comprising:
    a flexible structure;
    a plurality of fibers affixed to the structure, the fibers adapted to promote tissue ingrowth around the structure sufficient to provide permanent sterilization when disposed in a fallopian tube;
    an elongate body having a proximal end and a distal end, the elongate body releasably supporting the flexible structure within the distal end; and
    a hysteroscope through which the distal end of the elongate body is extendible while the hysteroscope is inserted transcervically, the hysteroscope providing an image from within the uterus to direct the elongate body laterally toward an ostium of the fallopian tube.

2. The system of claim 1, wherein the fibers induce tissue ingrowth when the flexible structure and fibers are advanced into the ostium and detached from the elongate body therein.

3. The system of claim 2, wherein the fibers comprise a polyester material.

4. The system of claim 2, wherein the structure has a first cross-section when supported by the elongate body and can define a second cross-section when deployed, the second cross-section being larger than the first cross-section.

* * * * *